United States Patent [19]
Hymanson

[11] Patent Number: 5,989,226
[45] Date of Patent: Nov. 23, 1999

[54] SYRINGE WITH DETACHABLE DRUG HOUSING

[75] Inventor: Victor Hymanson, Manchester, United Kingdom

[73] Assignee: Seldoren Limited, Lancashire, United Kingdom

[21] Appl. No.: 08/635,978

[22] PCT Filed: Nov. 10, 1994

[86] PCT No.: PCT/GB94/02475

§ 371 Date: May 9, 1996

§ 102(e) Date: May 9, 1996

[87] PCT Pub. No.: WO95/13842

PCT Pub. Date: May 26, 1995

[30] Foreign Application Priority Data

Nov. 13, 1993 [GB] United Kingdom .................. 9323447

[51] Int. Cl.$^6$ .................................................. A61M 5/32
[52] U.S. Cl. .......................... 604/198; 604/110; 604/232
[58] Field of Search .................................. 609/192, 197, 609/198, 206, 201, 232–235; 604/195, 198, 232, 234, 110

[56] References Cited

U.S. PATENT DOCUMENTS

| | | |
|---|---|---|
| 2,646,798 | 7/1953 | Brown ...................................... 604/234 |
| 2,671,450 | 3/1954 | Dann . |
| 2,778,359 | 1/1957 | Friedman . |
| 3,080,866 | 3/1963 | Friedman . |
| 3,583,399 | 6/1971 | Ritsky ...................................... 604/232 |
| 3,811,441 | 5/1974 | Sarnoff .................................... 604/234 |
| 3,825,002 | 7/1974 | Paige . |
| 4,738,663 | 4/1988 | Bogan ...................................... 604/198 |
| 5,057,088 | 10/1991 | Narayanan et al. ..................... 604/198 |
| 5,092,853 | 3/1992 | Couvertier, II ......................... 604/195 |
| 5,106,380 | 4/1992 | Lobello .................................... 604/198 |
| 5,129,884 | 7/1992 | Dysarz ...................................... 604/164 |
| 5,135,510 | 8/1992 | Maszkiewicz et al. ................. 604/195 |
| 5,256,153 | 10/1993 | Hake ........................................ 604/198 |
| 5,304,149 | 4/1994 | Morigi ..................................... 604/192 |
| 5,403,288 | 4/1995 | Stanners .................................. 604/232 |
| 5,445,620 | 8/1995 | Haber et al. ............................ 604/232 |
| 5,573,514 | 11/1996 | Stiehl et al. ............................ 604/198 |
| 5,674,203 | 10/1997 | Lewandowski ...................... 604/198 X |

FOREIGN PATENT DOCUMENTS

WO 89/04680 6/1989 WIPO .

*Primary Examiner*—Wynn Wood Coggins
*Assistant Examiner*—A. T. Nguyen
*Attorney, Agent, or Firm*—Fisher, Christen & Sabol

[57] ABSTRACT

A syringe has a drug-containing cartridge with a bung at one end which is engaged by a plunger, and a membrane at its other end which is penetrated by a needle. A connecting structure is connected to (or is formed integrally with) the needle and fits onto the forward end of the cartridge and the syringe. After use the cartridge, the connecting structure and the needle can be disposed together. A sleeve is slidably mounted on the structure and can be moved to sheath the needle.

18 Claims, 4 Drawing Sheets

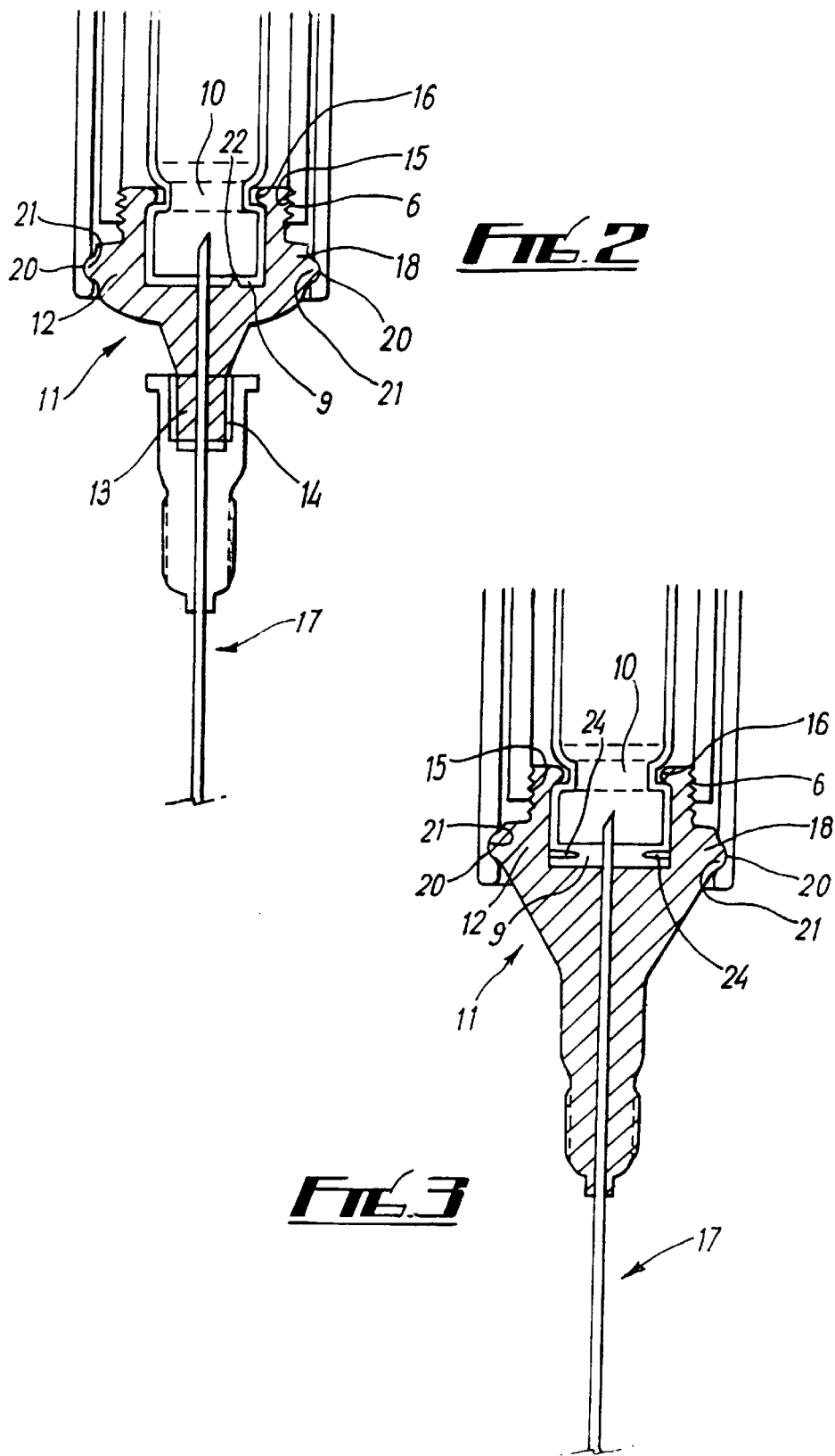

SYRINGE WITH DETACHABLE DRUG HOUSING

This invention relates to syringes.

A conventional syringe, e.g. as used by a dentist to administer anaesthetic, has a barrel with a plunger mechanism at one end and a threaded connector for a needle at the opposite end. A drug-containing glass cartridge is inserted into the barrel, the needle is screwed onto the connector so that it penetrates a seal at the forward end of the cartridge, and the plunger mechanism is operated to engage a bung at the rearward end of the cartridge and thereby expel the drug through the needle. After use, the needle and cartridge are removed and discarded.

In order to minimise contamination problems, European Application EP 0394295-A describes a syringe in which, in place of the above mentioned cartridge, there is a drug-containing housing which is attached directly to the needle at one end and to the plunger mechanism at the other end. After use the entire housing, including the needle, is detached from the plunger mechanism and discarded thereby avoiding the need to sterilise the barrel and needle connector of the conventional syringe.

Whilst this arrangement provides an effective solution to contamination problems, it is necessary for the specially-constructed detachable housing to be pre-filled with the drug which can be inconvenient from a manufacturing point of view.

An object of the present invention is to provide a disposable syringe housing which is convenient to manufacture.

According to one aspect of the invention therefore there is provided a detachable housing for a syringe comprising a drug-containing cartridge having a bung at one end and a penetrable member at the other end, the cartridge being adapted for connection to a needle at the said other end, such that the needle penetrates the penetrable member, and being adapted for connection to a plunger mechanism at the said one end, so that the bung can be moved down the cartridge to expel the drug through the needle, characterised in that the cartridge is provided with at least one separate structure attachable relative thereto, said structure being adapted for the said connection of the cartridge to the needle and providing means for releasable connection to the plunger mechanism, whereby the housing comprising the cartridge, the (or each) said structure, and the needle can be detached from the plunger mechanism for disposal together.

With this arrangement the advantages of disposability can be attained with an arrangement which is particularly simple and convenient to manufacture in so far as it involves the use of a simple drug-containing cartridge which may be of the kind used with conventional syringes.

Most preferably there is one said structure which is attachable to the said other end of the cartridge and which is adapted for connection to the needle and which provides the means for connection to the plunger mechanism.

Thus, and in accordance with a second aspect of the present invention there is provided a structure for attachment to a drug-containing cartridge of a syringe, which cartridge has a bung at a rearward end and a penetrable membrane at a forward end, said structure being adapted for attachment to a needle and having means for attachment relative to the forward end of the cartridge, and means for attachment to a plunger mechanism.

The means for attachment to the cartridge may comprise a clip or constriction or the like which fits around a neck at the forward end of the cartridge, such neck being a feature of conventional cartridges.

The structure may be formed integrally with the needle or alternatively it may incorporate means for connection to the needle which may comprise a threaded boss or nipple.

The means for attachment to the plunger mechanism may comprise an outer peripheral retaining structure, such as a screw-thread, adapted to mate with a corresponding retaining structure at the end of a barrel extension on the plunger mechanism, which extension fits around the cartridge from the rearward to the forward end thereof.

The barrel extension may have a longitudinally movable sleeve which can be moved forwardly to sheath the needle after use. This sleeve may be removable and disposable with the housing.

If desired, provision may be made for aspiration, or slight suck back with the syringe so that it can be seen if a vein or artery has been penetrated, such penetration being revealed by suck back of blood.

Thus, the said structure may be provided with a spring arrangement which acts to urge the cartridge in a direction away from the needle, in conjunction with a releasable retention device bearing on the top rim of the cartridge. The spring arrangement may comprise a projection engageable with the resilient penetrable member of the cartridge, or an interposed spring means.

The invention will now be described further by way of example only and with reference to the accompanying drawings in which:

FIGS. 2 & 3 are enlarged axial sections of a bottom part of the arrangement of FIG. 1 showing alternative embodiments thereof.

Figure 1:
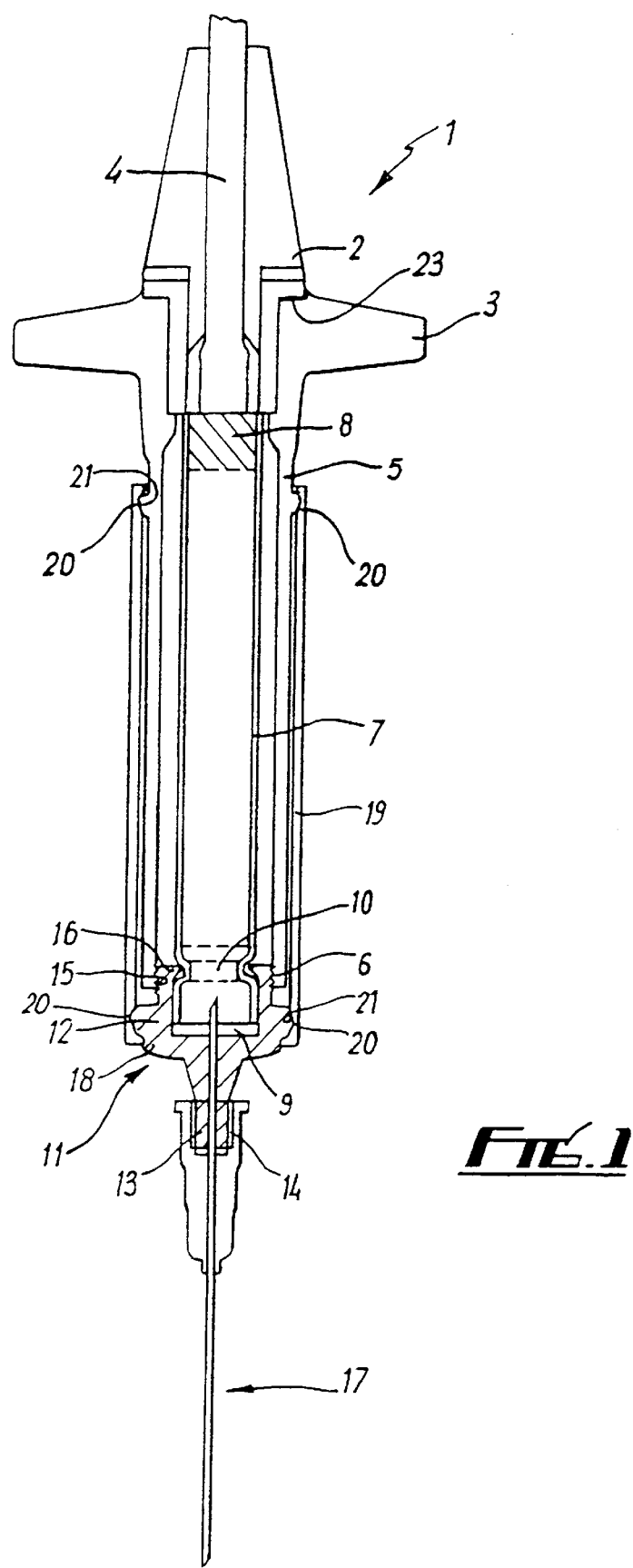
FIG. 1 is an axial section of a syringe provided with one form of a disposable housing in accordance with the invention.

Referring to FIG. 1, the syringe comprises a plunger mechanism 1 (e.g. of stainless steel) having a body part 2 with a finger grip 3, a plunger 4 slidable axially through a bore in the body 2, and a barrel extension 5 coaxial with the plunger 4. The barrel extension 5 may comprise a tube, or apertured tube, or tubular framework.

At its forward end, the tubular extension 5 has an internal screw-thread 6.

A conventional drug-containing cartridge 7 is used with the syringe, such cartridge comprising a glass tube with a bung 8 within one (rearward) end and a foil covered penetrable membrane 9 across the other (forward) end. The glass tube is shaped to provide a circumferential groove 10 defining a neck close to the forward end.

A connection structure 11 is attached to the forward end of the cartridge 7. This structure 11 comprises a plastics body of cup-shaped form with a cylindrical part 12 which is closed at one end and has a central axially projecting boss 13 on its outer face.

There is a narrow axial bore through the closed end and the boss 13. The boss 13 and the cylindrical part 12 both have external screw-threads 14, 15.

The cylindrical part 12 has an open end bounded by an inturned lip 16.

There is sufficient resilience in the lip 16 and/or the associated body of the connection structure 11 to enable the structure to be pushed over the forward end of the cartridge 7 so that the lip 16 springs into, or snap fits with, the groove 10 thereby to retain the structure 11 securely on the end of the cartridge 7.

With the connection structure 11 in position the cartridge 7 can be inserted into the barrel extension 5 and held securely in position by screwing the thread 15 of the cylindrical part 12 into engagement with the screw thread 6 at the end of the barrel extension 5.

A conventional needle 17 can then be screwed on to the boss 13 so that its rear end penetrates the membrane 9.

In this position the rearward end of the cartridge 7 is at the rearward end of the barrel extension 5 and the bung 8 is close to the end of the plunger 4.

The syringe can now be operated in the usual way to cause the bung 8 to be displaced down the cartridge 7 with the plunger 4 to expel drug through the needle 17.

After use, the connection structure 11 is unscrewed from the barrel extension 5 so that the cartridge 7, connection structure 11, and needle 17 can be removed and disposed together.

It will be seen that the cylindrical part 12 of the connection structure 11 has a lower, or forward portion 18 which is not threaded and which remains outside the barrel extension 5 to provide a convenient finger grip for screwing and unscrewing the structure 11. This portion 18 may be enlarged or shaped as desired to further facilitate gripping.

As shown in FIG. 1 a tubular sleeve 19 may be engaged around the connection structure 11, such sleeve 19 being movable axially between a rearward limit position (as shown) at which it overlies the barrel extension 5 and fully exposes the needle 17, and a forward limit position at which it covers the needle 17.

Figure 4:
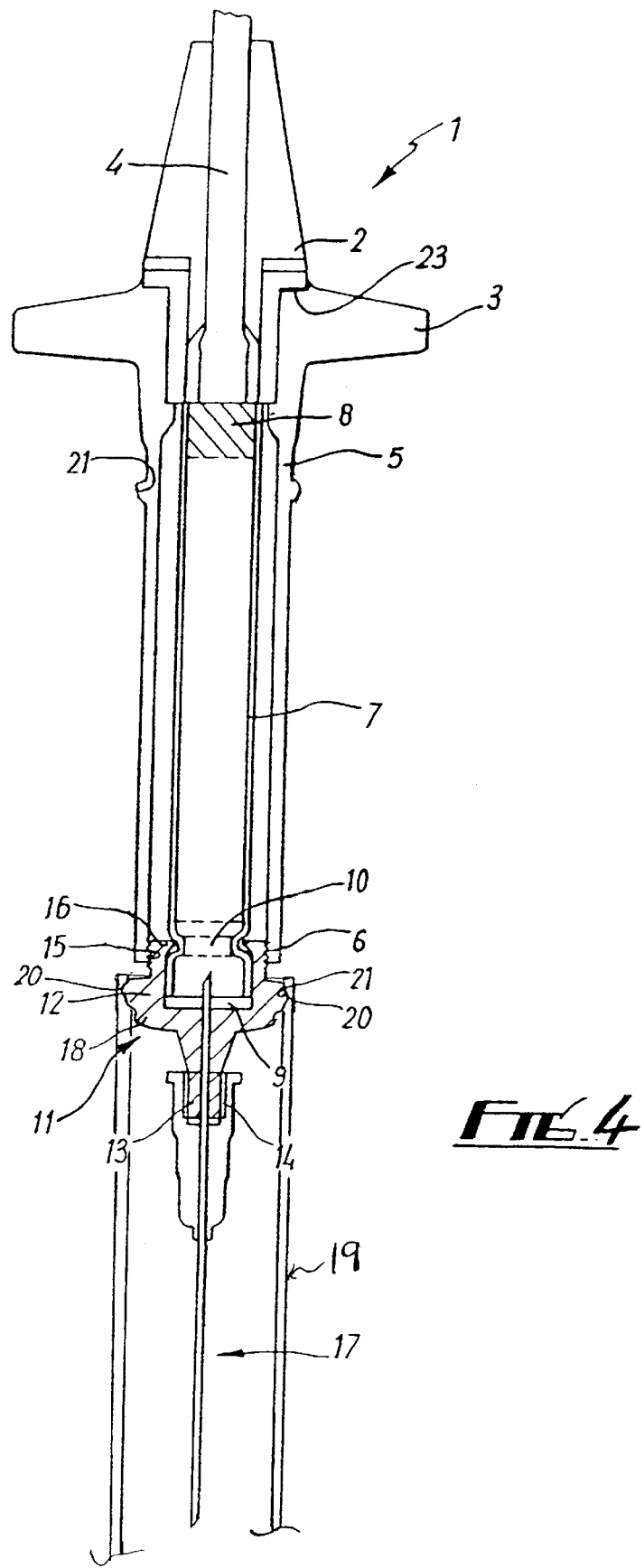
FIG. 4 is an axial section of the arrangement of FIG. 1 with the sleeve pushed forward.

FIG. 4 shows the arrangement of FIG. 1 with the sleeve (19) pushed fully forwardly to sheath the needle (17).

Figure 5:
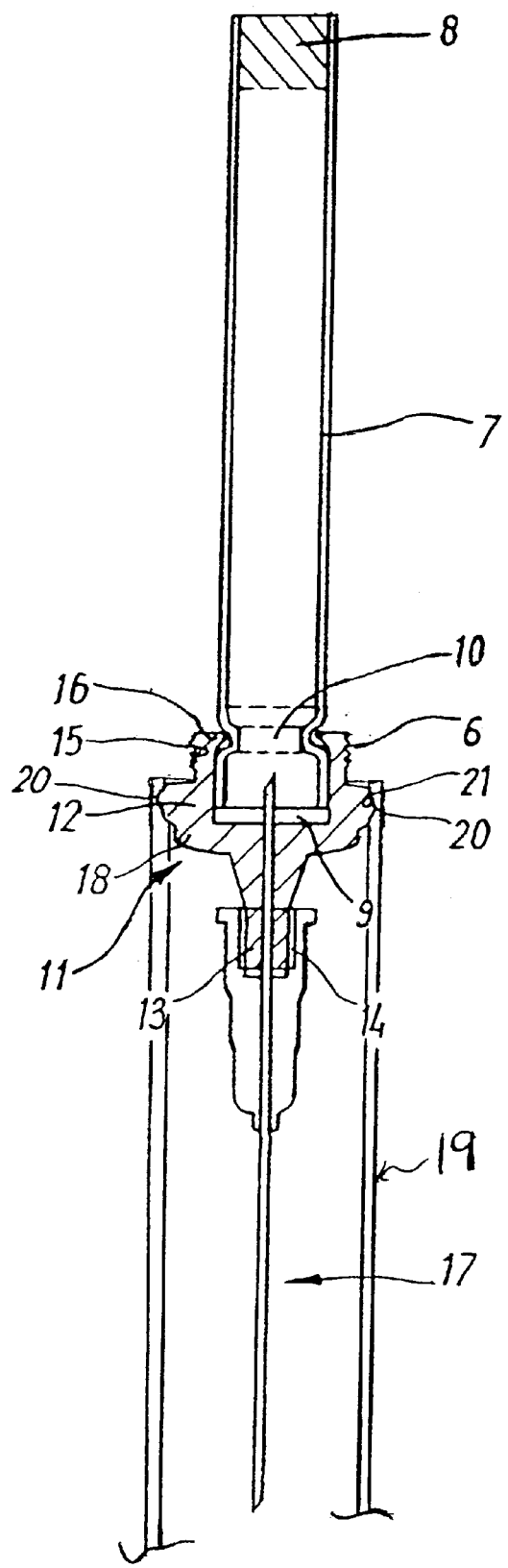
FIG. 5 is an axial section of the arrangement of FIG. 4 with the barrel and plunger mechanism detached.

FIG. 5 shows the arrangement of FIG. 4 with the barrel (5) and plunger mechanism (1) of the syringe detached so that the cartridge (7), mounting structure (11), needle (17) and sleeve (19) can be discarded together with the needle (17) protected at its forward end by the sleeve (19) and its rear end by the tubular rear part (12, 16) of the mounting structure (11), even if the cartridge (7) becomes detached.

The sleeve 19 is removed and disposed together with cartridge 7 and needle 17 with the sleeve 19 covering the needle 17 to avoid needle stick injuries.

The sleeve 19 has inwardly directed recesses 20 at each end which snap fit with projections 21 on the structure 11 to hold the sleeve 19 in each limit position. Also, the sleeve 19 may be internally longitudinally grooved to accommodate the projections 21 whereby the sleeve 19 is free to move axially but cannot rotate relative to the structure 11. The rotation of the structure 11 relative to barrel extension 5 can therefore be effected by rotation of the sleeve 19.

With the arrangement described above, full advantages of disposability can be attained using a conventional cartridge.

As shown in the modified embodiment of FIG. 2, the structure 11 has an upstanding small projection 22 which presses against the penetrable membrane 9 at the end of the cartridge. At the top end of the syringe there is a suitable structure (indicated diagrammatically at 23 in FIG. 1) which bears against the top rim of the cartridge and holds the projection 22 pressed firmly into the membrane 9.

If this top end bearing structure 23 is now released, and pressure is released from the plunger 4, the cartridge will move slightly upwards due to the resilience of the membrane 9. This gives a very small suck-back or aspiration effect through the needle.

This is useful e.g. in dentistry where an injection is being made into soft gum tissue and it is desired to avoid penetration of a vein or artery. If penetration of a vein or artery has occurred the aspiration will cause blood to flow back into the cartridge.

Other resilient or spring arrangements may be used to achieve aspiration. Thus, FIG. 3 shows a modification in which the structure 11 is formed integrally with the needle 17. Springy transverse projections 24 or fingers are incorporated for resilient engagement with the bottom of the cartridge.

It is of course to be understood that the invention is not intended to be restricted to the details of the above embodiment which are described by way of example only.

Thus, for example, the embodiment of FIG. 1 utilises a conventional needle and therefore has said connection structure 11 which is separate from the needle and is adapted to be interconnected thereto by means of the threaded boss 13. However, if desired, and as shown in FIG. 3, the structure 11 may be formed integrally with the needle so that it is supplied together with the needle.

Where the structure 11 is interconnected by means of the threaded boss 13 with a conventional needle, the structure 11 may be supplied with the needle, or ready fitted on the end of the cartridge or as a separate part to be fitted to the needle and to the cartridge prior to use.

The syringe may be as described adapted for end loading of the cartridge. It is however also possible to use a conventional side-loading syringe. The body of the syringe may be formed from plastics or stainless steel or any other suitable material or combination of materials as appropriate.

The interconnection between the structure 11 and the syringe body need not be through screw threads. Especially in the case of a rigid stainless steel syringe body, the interconnection may be achieved in the manner of a push-in or snap-fit or other clip type connection.

Depending on the nature of the syringe and the mode of location of the cartridge therewithin, the structure 11 need not clip around or otherwise connect positively to or even engage the end of the cartridge. The cartridge may be held within the body of the syringe in conventional manner e.g. after side loading thereof through the usual side slot or aperture.

I claim:

1. A syringe comprising a barrel having a front and a rearward end, and a detachable drug housing comprising a sleeve and a mounting structure, said barrel comprising at the front end a retaining structure with means to mate with a corresponding retaining structure of said mounting structure, said mounting structure comprising means for connecting a separate detachable needle to said mounting structure, an outer peripheral retaining structure with means to mate with said retaining structure at the forward end of the barrel, and projections, said sleeve having a forward end and a rear end and being mounted on said mounting structure for axial movement between a rearward operational position and a forward operational position, said sleeve further comprising, at its rear end, interlocking means to interlock with said projections of the mounting structure and to retain the sleeve in the forward operational position, whereby said drug housing comprising said sleeve and said mounting structure can be detached from said barrel while the projections of said mounting structure are interlocked with said interlocking means of the sleeve in its forward operational position.

2. A syringe according to claim 1, wherein said mounting structure comprises a lip which snap fits with a neck of a drug-containing cartridge.

3. A syringe according to claim 1, wherein said mounting structure is formed integrally with the needle.

4. A syringe according to claim 1 further comprising a spring arrangement on the mounting structure which acts on one end of a drug containing cartridge to urge the drug-containing cartridge in a direction away from the needle, and a resealable retention device to bear on a top rim of the drug containing cartridge located on the other end of the drug containing cartridge to resist said urging of the spring arrangement.

5. A syringe according to claim 2 further comprising a spring arrangement on the mounting structure which acts on one end of a drug containing cartridge to urge the drug-containing cartridge in a direction away from the needle, and a resealable retention device to bear on a top rim of the drug containing cartridge located on the other end of the drug containing cartridge to resist said urging of the spring arrangement.

6. A syringe according to claim 3 further comprising a spring arrangement on the mounting structure which acts on one end of a drug containing cartridge to urge the drug-containing cartridge in a direction away from the needle, and a resealable retention device to bear on a top rim of the drug containing cartridge located on the other end of the drug containing cartridge to resist said urging of the spring arrangement.

7. A syringe according to claim 1, wherein said retaining structure located at the front end of said barrel is selected from snap-fit, push-in, or clip connection retaining structures.

8. A syringe as claimed in claim 1, wherein said interlocking means of the sleeve interlocks with said projections of the mounting structure in a snap-fit interlocking arrangement.

9. A syringe as claimed in claim 1, wherein said interlocking means of the sleeve interlocks with said projections of the mounting structure by axial movement of said sleeve into the forward operational position.

10. A syringe as claimed in claim 9, wherein said interlocking means of the sleeve interlocks with said projections of the mounting structure without rotating of the sleeve relative to said mounting structure.

11. A disposable, detachable housing for a syringe comprising:
a mounting structure and a sleeve, said sleeve having a rear end and a forward end,
said mounting structure comprising means for connecting a separate detachable needle to said mounting structure, an outer peripheral retaining structure with means to mate with a corresponding retaining structure of a syringe barrel, a tubular structure with means to fit around a neck of a drug containing cartridge, and projections,
said sleeve being mounted on said mounting structure for axial movement between a rearward operational position and a forward operational position, and to interlock with said projections of the mounting structure and to retain the sleeve in the forward operational position by axial movement of said sleeve into the forward operational position without rotation of the sleeve relative to the mounting structure,
whereby said housing comprising the mounting structure and the sleeve are detachable from the syringe barrel for disposal while the projections of said mounting structure are interlocked with said interlocking means of the sleeve in its forward operational position.

12. A disposable, detachable housing for a syringe according to claim 11, wherein said sleeve interlocks with said projections of the mounting structure in a snap-fit Interlocking arrangement.

13. A disposable, detachable housing for a syringe according to claim 11, wherein said mounting structure comprises a lip which snap fits with a neck of the drug-containing cartridge.

14. A syringe according to claim 13 further comprising a spring arrangement on the mounting structure which acts on one end of the drug containing cartridge to urge the drug-containing cartridge in a direction away from the needle, and a resealable retention device to bear on a top rim of the drug containing cartridge located on the other end of the drug containing cartridge to resist said urging of the spring arrangement.

15. A disposable, detachable housing for a syringe according to claim 11, wherein said mounting structure is formed integrally with the needle.

16. A syringe according to claim 15 further comprising a spring arrangement on the mounting structure which acts on one end of the drug containing cartridge to urge the drug-containing cartridge in a direction away from the needle, and a resealable retention device to bear on a top rim of the drug containing cartridge located on the other end of the drug containing cartridge to resist said urging of the spring arrangement.

17. A disposable, detachable housing for a syringe according to claim 11 further comprising a spring arrangement on the mounting structure which acts on one end of the drug containing cartridge to urge the drug-containing cartridge in a direction away from the needle, and a resealable retention device to bear on a top rim of the drug containing cartridge located on the other end of the drug containing cartridge to resist said urging of the spring arrangement.

18. A syringe comprising a disposable, detachable housing for a syringe according to claim 11.

\* \* \* \* \*